United States Patent [19]

Uegai et al.

[11] 4,310,533

[45] Jan. 12, 1982

[54] GUANIDINOBENZOIC ACID DERIVATIVES

[75] Inventors: Yoshiaki Uegai, Ibaraki; Tsuyoshi Watanabe, Kadoma; Masashi Shiota, Nishinomiya; Itsuo Okumoto, Ashiya; Naohiro Kayama, Takatsuki, all of Japan

[73] Assignee: Ono Pharmaceutical Co., Ltd., Osaka, Japan

[21] Appl. No.: 182,513

[22] Filed: Aug. 29, 1980

[30] Foreign Application Priority Data

Aug. 31, 1979 [JP] Japan .................................. 54/110470

[51] Int. Cl.³ ................... A61K 31/445; C07C 101/68
[52] U.S. Cl. ................... 424/267; 260/326.43; 260/501.12; 544/58.1; 544/165; 542/427; 546/226; 546/328; 424/246; 424/248.55; 424/274; 424/310; 560/34; 424/256; 424/263
[58] Field of Search .................. 560/34; 260/326.43; 260/501.12; 546/226, 328; 544/162, 58.1, 165; 424/310, 246, 256, 263, 248.55, 267, 274; 542/427

[56] References Cited

U.S. PATENT DOCUMENTS 4,021,472 3/1977 Fujii et al. ............................ 560/34

*Primary Examiner*—G. T. Breitenstein
*Attorney, Agent, or Firm*—Sughrue, Mion, Zinn, Macpeak & Seas

[57] ABSTRACT

The guanidinobenzoic acid derivatives of the general formula:

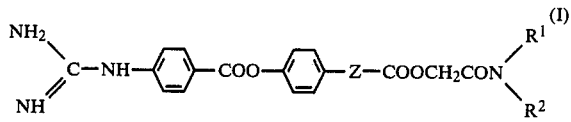

wherein Z represents a carbon-carbon covalent bond, or a methylene, ethylene or vinylene group, $R^1$ represents a hydrogen atom, or a straight- or branched-chain alkyl group containing from 1 to 4 carbon atoms, $R^2$ represents a straight- or branched-chain alkyl group containing from 4 to 10 carbon atoms, or a cycloalkyl or cycloalkenyl or straight- or branched-chain alkenyl group containing from 3 to 8 carbon atoms, or a phenyl or benzyl group, or $NR^1R^2$ represents a 4- to 8-membered heterocyclic ring, and acid addition salts thereof, have anti-plasmin and anti-trypsin activities.

9 Claims, No Drawings

GUANIDINOBENZOIC ACID DERIVATIVES

BACKGROUND OF THE INVENTION

1. Field of the Invention

This invention relates to new guanidinobenzoic acid derivatives, to processes for their preparation, and to pharmaceutical compositions containing them as an active ingredient.

2. Description of the Prior Art

A number of compounds are known to have antiplasmin and anti-trypsin activities. For example, trans-4-aminomethylcyclohexanecarboxylic acid as described in S. Okamoto and U. Okamoto, *Keio Journal of Medicine*, 11, 105 (1962) is known to be an anti-plasmin agent. "Trasylol" as described in B. Kassal et al., *J. Bio. Chem.*, 238, 3274 (1963) and German Patent Application (OLS) No. 1,905,813 is known to be an anti-trypsin agent, and the compounds described in U.S. Pat. No. 4,021,472 are known to be both anti-plasmin and anti-trypsin agents.

However, trans-4-aminomethylcyclohexanecarboxylic acid and "Trasylol" have disadvantages because they exhibit relatively low activities. The compounds described in U.S. Pat. No. 4,021,472 provide the same anti-plasmin or anti-trypsin effect at a lower dosage level than can be achieved with trans-4-aminomethylcyclohexanecarboxylic acid and "Trasylol". However, there has been an increasing demand for compounds even more potent at a lower dosage level since reduced dosage generally means lowered side effects which is desirable from the standpoint of safety.

SUMMARY OF THE INVENTION

As a result of extensive research on anti-plasmin and anti-trypsin agents, it has now been found that a new series of guanidinobenzoic acid derivatives have anti-plasmin and anti-trypsin activities.

Accordingly, the present invention resides in one aspect in guanidinobenzoic acid derivatives of the general formula:

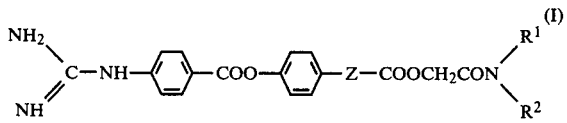

(wherein Z represents a carbon-carbon covalent bond, or a methylene, ethylene or vinylene group, $R^1$ represents a hydrogen atom, or a stright- or branched-chain alkyl group containing from 1 to 4 carbon atoms, $R^2$ represents a straight- or branched-chain alkyl group containing from 4 to 10 carbon atoms, or a cycloalkyl or cycloalkenyl or straight- or branched-chain alkenyl group containing from 3 to 8 carbon atoms, or a phenyl or benzyl group, or $NR^1R^2$ represents a 4- to 8-membered heterocyclic ring), and acid addition salts thereof.

The invention further resides in processes for the preparation of the guanidinobenzoic acid derivatives in the preceding paragraph and to pharmaceutical compositions containing the derivatives as an active ingredient.

DETAILED DESCRIPTION OF THE INVENTION

Examples of the alkyl group containing from 1 to 4 carbon atoms represented by $R^1$ are methyl, ethyl, propyl, isopropyl, butyl, isobutyl, sec-butyl and tert-butyl.

Examples of the alkyl group containing from 4 to 10 carbon atoms represented by $R^2$ are butyl, pentyl, hexyl, heptyl, octyl, nonyl, decyl, and their isomers.

Examples of the cycloalkyl, cycloalkenyl and alkenyl group containing from 3 to 8 carbon atoms represented by $R^2$ are cyclopropyl, cyclobutyl, cyclopentyl, cyclohexyl, cycloheptyl, cyclooctyl, 3-cyclopentenyl, 2-cyclohexenyl, 3-cyclohexenyl, allyl, 2-butenyl, 3-butenyl, 3-methyl-2-butenyl, 2-methylallyl, 1-pyrrolidinyl, piperidino, 1-pyrrolyl, morpholino, thiamorpholino, and aza-2,5-cyclohexadienyl.

Preferably, $R^2$ is a cycloalkyl or cycloalkenyl or straight- or branched-chain alkenyl group containing from 3 to 8 carbon atoms, or a phenyl or benzyl group, or an $NR^1R^2$ is a 4- to 8-membered heterocyclic ring.

Preferably, the group

is N-butyl, N-sec-butyl, N-pentyl, N-octyl, N-methyl-N-butyl, N-methyl-N-hexyl, N-ethyl-N-butyl, N-propyl-N-butyl, N-cyclopropyl, N-cyclobutyl, N-cyclopentyl, N-cyclohexyl, N-cycloheptyl, N-cyclooctyl, N-methyl-N-cyclopentyl, N-methyl-N-cyclohexyl, N-phenyl, N-benzyl, piperidino, 1-pyrrolidinyl, morpholino and N-allyl.

Preferably, Z is a carbon-carbon covalent bond.

According to a feature of the present invention, the guanidinobenzoic acid derivatives of general formula (I), wherein the various symbols are as hereinbefore defined, are prepared by reacting a compound of the general formula:

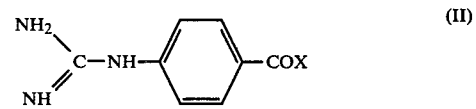

(wherein X represents a halogen atom) or an acid addition salt thereof with a compound of the general formula:

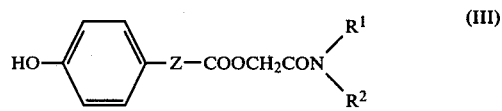

(wherein Z, $R^1$ and $R^2$ are as hereinbefore defined) in the presence of a dehydrohalogenating agent in an inert solvent at a temperature from ambient to $-20°$ C. for 1 to 5 hours.

Suitable examples of the dehydrohalogenating agent, which can be used in the above reaction, are tertiary amines such as triethylamine, tributylamine, N,N-dimethylaniline, N-methylpiperidine, pyridine and the like.

Suitable examples of the solvent are benzene, toluene, diethyl ether, tetrahydrofuran, dioxane, acetone, acetonitrile, pyridine, N,N-dimethylformamide and the like, or a mixture of two or more of them, especially the pyridine is preferred because it is used as a solvent and as a dehydrohalogenating agent.

The reaction product is obtained in a form of an acid addition salt, and may be isolated as such, or may be obtained as crystals precipitated by adding an aqueous solution of sodium bicarbonate to the reaction mixture, or to the residue obtained by distilling away the reaction solvent under reduced pressure, or to the residual oil obtained by removal of the reaction solvent with a solvent in which the reaction product is insoluble.

The compounds of general formula (I) can, if desired, be easily converted to pharmaceutically acceptable acid addition salts. Suitable examples of the acid are inorganic acids such as hydrochloric acid, hydrobromic acid, sulfuric acid, phosphoric acid, nitric acid and the like, and organic acids such as acetic acid, lactic acid, oxalic acid, maleic acid, fumaric acid, succinic acid, tartaric acid, malic acid, citric acid, benzenesulfonic acid, toluenesulfonic acid, methanesulfonic acid and the like. Preferred examples of pharmaceutically acceptable acid addition salts of the compounds of general formula (I) are methanesulfonates, toluenesulfonates, hydrochlorides, and phosphates.

The compounds of general formula (II) or acid addition salts thereof can be prepared from 4-guanidinobenzoic acid by conventional means. For example, 4-guanidinobenzoic acid is heated with thionyl chloride to give 4-guanidinobenzoyl chloride hydrochloride, which is used in the next reaction.

The compounds of general formula (III) may be prepared by reacting a compound of the general formula:

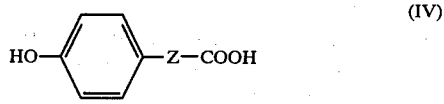

(IV)

(wherein Z is as hereinbefore defined) with a compound of the general formula:

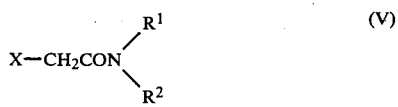

(V)

(wherein X, $R^1$ and $R^2$ are as hereinbefore defined) in the presence of a dehydrohalogenating agent such as triethylamine or tributylamine in an inert organic solvent such as acetonitrile, tetrahydrofuran, benzene, toluene, or N,N-dimethylformamide at a temperature from ambient to 150° C. for 2 to 20 hours.

The compounds of general formulae (IV) and (V) are well known, or may easily be prepared by methods known per se. By the term "methods known per se" as used in this specification is meant methods heretofore used or described in the chemical literature.

The compounds of the present invention are new compounds, which have inhibitory activities on proteinase trypsin and plasmin, and their inhibitory activities were strongly observed at very low concentrations in the case of trypsin and plasmin.

Furthermore, the compounds of the present invention are excellent in solubility and, therefore, are suitable for administration as a human medicine in the form of an aqueous solution, saline, aqueous glucose or other solutions.

The inhibitory activities on trypsin and plasmin in vitro were determined by the methods of M. Muramatsu et al. described in the *Journal of Biochemistry*, 58, 214 (1965) for trypsin, and ibid., 57, 402 (1964) for plasmin, and the results are shown in Table 1

TABLE 1

| Compound No. | 50% Inhibition Concentration (molar concentration) | | Solubility in Water |
|---|---|---|---|
| | Anti-Trypsin[1] | Anti-Plasmin[2] | |
| 1 | $5.0 \times 10^{-10}$M | $4.5 \times 10^{-10}$M | 20 mM |
| 2 | $1.8 \times 10^{-10}$M | $1.3 \times 10^{-10}$M | 20 mM |
| 3 | — | $3.0 \times 10^{-5}$M | — |
| 4 | $2.8 \times 10^{-6}$M | — | — |

Compound No. 1: Piperidinocarbonylmethyl 4-(4-guanidinobenzoyloxy)benzoate mesylate
Compound No. 2: N-Cyclohexylcarbamoylmethyl 4-(4-guanidinobenzoyloxy)benzoate mesylate
Compound No. 3: trans-4-Aminomethylcyclohexanecarboxylic acid
Compound No. 4: "Trasylol"
[1]The concentration of the compounds represented by the general formula (I) at which the activity of trypsin 0.5 μg to hydrolyze p-tosylarginine methyl ester was 50% inhibited, when treated at 37° C. for 30 minutes.
[2]The concentration of the compounds represented by the general formula (I) at which the activity of plasmin was 50% inhibited, when reacted in a system comprising 0.1 ml of human-euglobulin (10 fold dilution), 0.1 ml of streptokinase (2,000 unit/ml), 0.4 ml of fibrinogen (4% solution), 0.3 ml of a 0.1M borate saline buffer solution (pH 7.4) and 0.1 ml of a solution of each of the compounds at 37° C. for 30 minutes.

As is apparent from the above results, the guanidinobenzoic acid derivatives or acid addition salts thereof have strongly inhibitory activity on proteinase trypsin and plasmin and thus are useful as a drug for treating acute pancreatitis and the like, or as an anti-plasmin drug for treating bleeding disorders and the like.

This invention also includes in its scope pharmaceutical compositions comprising at least one of the compounds of general formula (I) or pharmaceutically acceptable acid addition salts thereof and pharmaceutically acceptable carriers, diluents and excipients.

Usually the compounds or pharmaceutical compositions comprising the same are administered orally. Suitable examples of solid formulations for oral administration include tablets, pills, powders and granules. In these solid formulations one or more active ingredients are mixed with at least one inactive diluent such as calcium carbonate, potato starch, alginic acid, lactose, etc. The formulation may contain additives other than the diluents, for example, lubricants such as magnesium stearate, etc.

Suitable examples of liquid formulations for oral administration include pharmaceutically acceptable emulsions, solutions, suspensions, syrups or elixirs. Conventionally used liquid diluents are, for example, water or liquid paraffin. This formulation may also contain, in addition to the diluents, auxiliary agents, for example, humectants, suspension aids, sweeteners, flavors, fragrants or antiseptics.

Capsules comprising an assimilable substance such as gelatin and which contain one or more active ingredients and a diluent or an excipient can also be used in this invention as a suitable example of formulation for oral administration.

In this invention the amount of the active ingredient in the formulation can be varied and a suitable amount is determined depending on the therapeutic purpose. Dosage is determined based on the therapeutic effects desired, the number of times administered and the period of treatment.

Usually, the dosage for an adult is about 100 mg to about 1 g for treating acute pancreatitis and hemorrhagic diseases by oral administration.

Examples of the guanidinobenzoic acid derivatives of the general formula (I) considered within the present invention are N-butylcarbamoylmethyl 4-(4-guanidinobenzoyloxy)benzoate, N-sec-butylcarbamoylmethyl 4-(4-guanidinobenzoyloxy)benzoate, N-pentylcarbamoylmethyl 4-(4-guanidinobenzoyloxy)benzoate, N-octylcarbamoylmethyl 4-(4-guanidinobenzoyloxy)benzoate, N-methyl-N-butylcarbamoylmethyl 4-(4-guanidinobenzoyloxy)benzoate, N-methyl-N-hexylcarbamoylmethyl 4-(4-guanidinobenzoyloxy)benzoate, N-ethyl-N-butylcarbamoylmethyl 4-(4-guanidinobenzoyloxy)benzoate, N-propyl-N-butylcarbamoylmethyl 4-(4-guanidinobenzoyloxy)benzoate, N-cyclopropylcarbamoylmethyl 4-(4-guanidinobenzoyloxy)benzoate, N-cyclobutylcarbamoylmethyl 4-(4-guanidinobenzoyloxy)benzoate, N-cyclopentylcarbamoylmethyl 4-(4-guanidinobenzoyloxy)benzoate, N-cyclohexylcarbamoylmethyl 4-(4-guanidinobenzoyloxy)benzoate, N-cycloheptylcarbamoylmethyl 4-(4-guanidinobenzoyloxy)benzoate, N-cyclooctylcarbamoylmethyl 4-(4-guanidinobenzoyloxy)benzoate, N-methyl-N-cyclopentylcarbamoylmethyl 4-(4-guanidinobenzoyloxy)benzoate, N-methyl-N-cyclohexylcarbamoylmethyl 4-(4-guanidinobenzoyloxy)benzoate, N-phenylcarbamoylmethyl 4-(4-guanidinobenzoyloxy)benzoate, N-benzylcarbamoylmethyl 4-(4-guanidinobenzoyloxy)benzoate, piperidinocarbonylmethyl 4-(4-guanidinobenzoyloxy)benzoate, pyrrolidinylcarbonylmethyl 4-(4-guanidinobenzoyloxy)benzoate, morpholinocarbonylmethyl 4-(4-guanidinobenzoyloxy)benzoate, N-butylcarbamoylmethyl 4-(4-guanidinobenzoyloxy)phenylacetate, N-sec-butylcarbamoylmethyl 4-(4-guanidinobenzoyloxy)phenylacetate, N-hexylcarbamoylmethyl 4-(4-guanidinobenzoyloxy)phenylacetate, N-octylcarbamoylmethyl 4-(4-guanidinobenzoyloxy)phenylacetate, N-methyl-N-butylcarbamoylmethyl 4-(4-guanidinobenzoyloxy)phenylacetate, N-ethyl-N-butylcarbamoylmethyl 4-(4-guanidinobenzoyloxy)phenylacetate, N-cyclopropylcarbamoylmethyl 4-(4-guanidinobenzoyloxy)phenylacetate, N-cyclobutylcarbamoylmethyl 4-(4-guanidinobenzoyloxy)phenylacetate, N-cyclopentylcarbamoylmethyl 4-(4-guanidinobenzoyloxy)phenylacetate, N-cyclohexylcarbamoylmethyl 4-(4-guanidinobenzoyloxy)phenylacetate, N-cycloheptylcarbamoylmethyl 4-(4-guanidinobenzoyloxy)phenylacetate, N-cyclooctylcarbamoylmethyl 4-(4-guanidinobenzoyloxy)phenylacetate, N-methyl-N-cyclopentylcarbamoylmethyl 4-(4-guanidinobenzoyloxy)phenylacetate, N-methyl-N-cyclohexylcarbamoylmethyl 4-(4-guanidinobenzoyloxy)phenylacetate, N-phenylcarbamoylmethyl 4-(4-guanidinobenzoyloxy)phenylacetate, piperidinocarbonylmethyl 4-(4-guanidinobenzoyloxy)phenylacetate, pyrrolidinylcarbonylmethyl 4-(4-guanidinobenzoyloxy)phenylacetate, morpholinocarbonylmethyl 4-(4-guanidinobenzoyloxy)phenylacetate, N-butylcarbamoylmethyl 4-(4-guanidinobenzoyloxy)phenylpropionate, N-pentylcarbamoylmethyl 4-(4-guanidinobenzoyloxy)phenylpropionate, N-methyl-N-butylcarbamoylmethyl 4-(4-guanidinobenzoyloxy)phenylpropionate, N-cyclopentylcarbamoylmethyl 4-(4-guanidinobenzoyloxy)phenylpropionate, N-cyclohexylcarbamoylmethyl 4-(4-guanidinobenzoyloxy)phenylpropionate, N-cycloheptylcarbamoylmethyl 4-(4-guanidinobenzoyloxy)phenylpropionate, N-phenylcarbamoylmethyl 4-(4-guanidinobenzoyloxy)phenylpropionate, N-benzylcarbamoylmethyl 4-(4-guanidinobenzoyloxy)phenylpropionate, piperidinocarbonylmethyl 4-(4-guanidinobenzoyloxy)phenylpropionate, pyrrolidinylcarbonylmethyl 4-(4-guanidinobenzyloxy)phenylpropionate, morpholinocarbonylmethyl 4-(4-guanidinobenzoyloxy)phenylpropionate, N-butylcarbamoylmethyl 4-(4-guanidinobenzoyloxy)cinnamate, N-hexylcarbamoylmethyl 4-(4-guanidinobenzoyloxy)cinnamate, N-methyl-N-butylcarbamoylmethyl 4-(4-guanidinobenzoyloxy)cinnamate, N-cyclopentylcarbamoylmethyl 4-(4-guanidinobenzoyloxy)cinnamate, N-cyclohexylcarbamoylmethyl 4-(4-guanidinobenzoyloxy)cinnamate, N-cyclooctylcarbamoylmethyl 4-(4-guanidinobenzoyloxy)cinnamate, N-phenylcarbamoylmethyl 4-(4-guanidinobenzoyloxy)cinnamate, N-benzylcarbamoylmethyl 4-(4-guanidinobenzoyloxy)cinnamate, piperidinocarbonylmethyl 4-(4-guanidinobenzoyloxy)cinnamate, pyrrolidinylcarbonylmethyl 4-(4-guanidinobenzoyloxy)cinnamate, morpholinocarbonylmethyl 4-(4-guanidinobenzoyloxy)cinnamate, N-allylcarbamoylmethyl 4-(4-guanidinobenzoyloxy)benzoate, N-allylcarbamoylmethyl 4-(4-guanidinobenzoyloxy)phenylacetate, N-allylcarbamoylmethyl 4-(4-guanidinobenzoyloxy)phenylpropionate, and N-allylcarbamoylmethyl 4-(4-guanidinobenzoyloxy)cinnamate.

This invention is illustrated in further detail by reference to the following Examples, but it should be understood that they are given for illustrative purposes only and are not to be construed as limiting the scope of the invention.

REFERENCE EXAMPLE 1

Preparation of piperidinocarbonylmethyl 4-hydroxybenzoate

To 100 ml of acetonitrile were added 7.75 g of N-(α-chloroacetyl)piperidine, 5.0 g of 4-hydroxybenzoic acid and 4.3 g (5.9 ml) of triethylamine, and the mixture was refluxed with heating for 2 hours. The reaction mixture was filtered, and the filtrate was concentrated under reduced pressure. To the residue was added ice-water, and precipitated crystals were recrystallized from water to give 8.0 g of the title compound. Melting point: 160°–164° C.

REFERENCE EXAMPLE 2

Preparation of N-cyclohexylcarbamoylmethyl 4-hydroxybenzoate

To 120 ml of acetonitrile were added 8.78 g of N-cyclohexyl-α-chloroacetamide, 5.52 g of 4-hydroxybenzoic acid and 5.05 g (7.0 ml) of triethylamine, and the mixture was refluxed with heating for 2 hours, followed by treatment as described in Reference Example 1 to give 8.5 g of the title compound. Melting point: 131°–135° C.

EXAMPLE 1

Preparation of piperidinocarbonylmethyl 4-(4-guanidinobenzoyloxy)benzoate mesylate 5.4 g of 4-guanidinobenzoic acid and 50 ml of thionyl chloride were heated at 70° to 75° C. for 30 minutes with stirring. To the reaction mixture was added petroleum ether to precipitate crystals of 4-guanidinobenzoyl chloride hydrochloride, which were filtered and washed with petroleum ether. The 4-guanidinobenzoyl chloride, thus obtained, was added to 7.9 g of piperidinocarbonylmethyl 4-hydroxybenzoate in 100 ml of pyridine at 0° C., followed by stirring at 10° to 20° C. for 3 hours. To the reaction mixture was added diethyl ether, and the supernatant was removed by decantation, and then to the residual oil was added a saturated aqueous solution of sodium bicarbonate. The precipitated crystals were filtered off, washed successively with water and acetone, and dried. The obtained crystals were suspended in methanol, and the suspension was acidified at pH 3 by adding methanesulfonic acid, and then filtered. Diethyl ether was added to the filtrate to precipitate crystals. Recrystallization thereof from methanol afforded 8.4 g (70%) of the title compound as white crystals. Melting point: 189°–190° C.

Elemental analysis for $C_{15}H_{20}N_4O_3 \cdot CH_3SO_3H$: Calcd. (%): C, 47.99; H, 6.04; N, 13.99; S, 8.01: Found (%): C, 48.23; H, 6.25; N, 13.76; S, 7.79.

EXAMPLE 2

Preparation of N-cyclohexylcarbamoylmethyl 4-(4-guanidinobenzoyloxy)benzoate mesylate 4-Guanidinobenzoyl chloride hydrochloride was prepared from 4.5 g of 4-guanidinobenzoic acid by the same procedure as described in Example 1. It was added to a solution of 6.9 g of N-cyclohexylcarbamoylmethyl 4-hydroxybenzoate in 70 ml of pyridine at 0° C., and the mixture was stirred at 10° to 20° C. for 3 hours, followed by the treatment as described in Example 1 to give 6.9 g (67%) of the title compound as white crystals (recrystallized from methanol). Melting point: 154°–156° C.

Elemental analysis for $C_{16}H_{22}N_4O_3 \cdot CH_3SO_3H$: Calcd. (%): C, 49.26; H, 6.32; N, 13.52; S, 7.73: Found (%): C, 49.41; H, 6.18; N, 13.69; S, 7.87.

EXAMPLE 3

One thousand film-coated tablets for oral administration were prepared from the following compounds in manner known per se, each tablet containing 100 mg of the active ingredient.

| | |
|---|---|
| Piperidinocarbonylmethyl 4-(4-guanidinobenzoyloxy)benzoate mesylate | 100 g |
| Lactose | 13 g |
| Calcium carboxymethylcellulose | 4 g |
| Hydroxypropylcellulose | 2 g |
| Magnesium stearate | 1 g |
| Hydroxypropylcellulose (film-coating agent) | 8.6 g |
| Dimethylpolysiloxane (film-coating agent) | 0.85 g |

By proceeding as described above, but replacing the piperidinocarbonylmethyl 4-(4-guanidinobenzoyloxy)benzoate mesylate by 100 g of N-cyclohexylcarbamoylmethyl 4-(4-guanidinobenzoyloxy)benzoate mesylate, there were obtained one thousand film-coated tablets for oral administration, each tablet containing 100 mg of the active ingredient.

While the invention has been described in detail and with reference to specific embodiments thereof, it will be apparent to one skilled in the art that various changes and modifications can be made therein without departing from the spirit and scope thereof.

What is claimed is:

1. A guanidinobenzoic acid derivative of the general formula:

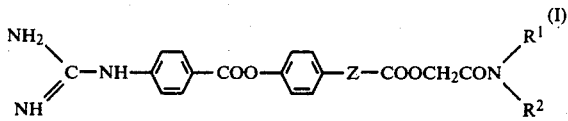

wherein Z represents a carbon-carbon covalent bond, or a methylene, ethylene or vinylene group, $R^1$ represents a hydrogen atom, or a straight- or branched-chain alkyl group containing from 1 to 4 carbon atoms, $R^2$ represents a cycloalkyl or cycloalkenyl group containing from 3 to 8 carbon atoms, or a phenyl or benzyl group, or $NR^1R^2$ represents a heterocyclic ring selected from the group consisting of 1-pyrrolidinyl, piperidino, 1-pyrrolyl, morpholino, thiamorpholino and aza-2,5-cyclohexadienyl rings, or an acid addition salt thereof.

2. A guanidinobenzoic acid derivative or an acid addition salt thereof according to claim 1 in which $R^2$ is a cycloalkyl or cycloalkenyl group containing from 3 to 8 carbon atoms, or a phenyl or benzyl group.

3. A guanidinobenzoic acid derivative or an acid addition salt thereof according to claim 1 in which $NR^1R^2$ is N-cyclopropyl, N-cyclobutyl, N-cyclopentyl, N-cyclohexyl, N-cycloheptyl, N-cyclooctyl, N-methyl-N-cyclopentyl, or N-methyl-N-cyclohexyl.

4. A guanidinobenzoic acid derivative according to claim 1 which is N-cyclohexylcarbamoylmethyl 4-(4-guanidinobenzoyloxy)benzoate, or an acid addition salt thereof.

5. A guanidinobenzoic acid derivative or an acid addition salt thereof according to claim 1 in which $NR^1R^2$ is a 1-pyrrolidinyl, piperidino, 1-pyrrolyl, morpholino, thiamorpholino, or aza-2,5-cyclohexadienyl ring.

6. A guanidinobenzoic acid derivative or an acid addition salt thereof according to claim 1 in which $NR^1R^2$ is piperidino, 1-pyrrolidinyl, or morpholino.

7. A guanidinobenzoic acid derivative according to claim 5 which is piperidinocarbonylmethyl 4-(4-guanidinobenzoyloxy)benzoate, or an acid addition salt thereof.

8. A guanidinobenzoic acid derivative according to claim 1, wherein the acid addition salt is a salt of hydrochloric acid, hydrobromic acid, sulfuric acid, phosphoric acid, nitric acid, acetic acid, lactic acid, oxalic acid, maleic acid, fumaric acid, succinic acid, tartaric acid, malic acid, citric acid, benzenesulfonic acid, toluenesulfonic acid, or methanesulfonic acid.

9. A method of inhibiting the activity of plasmin and/or trypsin which comprises administering a therapeutically effective amount of at least one guanidinobenzoic acid derivative as claimed in claim 1, or an acid addition salt thereof.

* * * * *